US011357866B2

(12) United States Patent
Braun et al.

(10) Patent No.: US 11,357,866 B2
(45) Date of Patent: Jun. 14, 2022

(54) EXPRESSION OF HIV INHIBITORS BY MESENCHYMAL STEM CELLS

(71) Applicant: The Administrators of the Tulane Educational Fund, New Orleans, LA (US)

(72) Inventors: Stephen E. Braun, New Orleans, LA (US); Debasis Mondal, New Orleans, LA (US); Bruce A Bunnell, New Orleans, LA (US); Narae Lee, New Orleans, LA (US)

(73) Assignee: THE ADMINISTRATORS OF THE TULANE EDUCATIONAL FUND, New Orleans, LA (US)

( * ) Notice: Subject to any disclaimer, the term of this patent is extended or adjusted under 35 U.S.C. 154(b) by 275 days.

(21) Appl. No.: 16/002,604

(22) Filed: Jun. 7, 2018

(65) Prior Publication Data

US 2018/0280538 A1    Oct. 4, 2018

Related U.S. Application Data

(63) Continuation-in-part of application No. 14/782,115, filed as application No. PCT/US2014/032832 on Apr. 3, 2014, now abandoned.

(60) Provisional application No. 61/808,097, filed on Apr. 3, 2013.

(51) Int. Cl.
| | |
|---|---|
| C12N 5/00 | (2006.01) |
| A61K 48/00 | (2006.01) |
| A61K 39/42 | (2006.01) |
| C07K 16/10 | (2006.01) |
| A61P 31/18 | (2006.01) |
| A61K 45/06 | (2006.01) |
| A61K 31/513 | (2006.01) |
| A61K 35/28 | (2015.01) |
| A61K 31/683 | (2006.01) |
| A61K 39/00 | (2006.01) |

(52) U.S. Cl.
CPC ............ *A61K 48/00* (2013.01); *A61K 31/513* (2013.01); *A61K 31/683* (2013.01); *A61K 35/28* (2013.01); *A61K 39/42* (2013.01); *A61K 45/06* (2013.01); *A61P 31/18* (2018.01); *C07K 16/1045* (2013.01); *A61K 2039/505* (2013.01); *C07K 2317/76* (2013.01); *C12N 2740/16043* (2013.01)

(58) Field of Classification Search
None
See application file for complete search history.

(56) References Cited

U.S. PATENT DOCUMENTS

| | | | |
|---|---|---|---|
| 7,041,293 B1 | 5/2006 | Berman | |
| 10,357,562 B2 * | 7/2019 | Garry | ...................... A61K 35/28 |
| 10,472,647 B2 * | 11/2019 | Tomchuck | .............. C12N 15/85 |
| 2010/0104580 A1 | 4/2010 | Chaiken | |
| 2010/0331527 A1 * | 12/2010 | Davis | .................. C07K 16/2809 530/387.3 |
| 2011/0027240 A1 | 2/2011 | Laer | |
| 2020/0123236 A1 * | 4/2020 | Guenaga | ................. A61P 31/18 |
| 2020/0206342 A1 * | 7/2020 | Procko | ................... A61K 39/21 |

FOREIGN PATENT DOCUMENTS

| | | |
|---|---|---|
| WO | 2009087110 | 7/2009 |
| WO | 2010053350 | 5/2010 |

OTHER PUBLICATIONS

McGinnes et al. Newcastle Disease Virus HN Protein Alters the Conformation of the F Protein at Cell Surfaces Journal of Virology, Dec. 2002, p. 12622-12633.*
Khan et al Targeting the HIV-1 Spike and Coreceptor with Bi- and Trispecific Antibodies for Single-Component Broad Inhibition of Entry 2018; JVC Issue 18 e00384-18; pp. 1-19.*
Burton et al Advancing an HIV vaccine; advancing vaccinology Nat Rev Immunol. Feb. 2019 ; 19(2): 77-78.*
Deng et al., Nature • vol. 381 • Jun. 20, 1996; pp. 661-666.*
Altanerova et al., Human adipose tissue-derived mesenchymal stem cells expressing yeast cytosinedeaminase::uracil phosphoribosyltransferase inhibit intracerebral rat glioblastoma Int. J. Cancer: 130, 2455-2463 (2012).*
Izadpanah et al., Gene delivery to mesenchymal stem cells 2008; Methods in Molecular Biology pp. 154-166.*
Eliopoulos et al Neo-Organoid of Marrow Mesenchymal Stromal Cells Secreting Interleukin-12 for Breast Cancer Therapy 2008; Cancer; pp. 4810-4818.*
Moreno et al 2011 The β-Interferon Scaffold Attachment Region Confers High-Level Transgene Expression and Avoids Extinction by Epigenetic Modifications of Integrated Provirus in Adipose Tissue-Derived Human Mesenchymal Stem Cells Tissue Engineering Part C, Tissue Engineering: Part C vol. 17, No. 3,pp. 275-287.*
Stagg et al., Mechanisms of Immune Modulation by Mesenchymal Stromal Cells and Clinical Translation Current Molecular Medicine, Current Molecular Medicine 2013, 13, 856-867 vol. 13, No. 5, 2013, pp. 856-867(12).*
Huang et al., Broad and potent HIV-1 neutralization by a human antibody that binds the gp41-120 interface Nature. Nov. 6, 2014; 515(7525): 138-142.*
Ahmad et al scFv Antibody: Principles and Clinical Application Clinical and Developmental Immunology vol. 2012, Article ID 980250, 15 pages.*
International Search Report for PCT counterpart PCT/US2014/032832, dated Aug. 27, 2014.
Thyagarajan et al., 2009; A single EBV-based vector for stable episomal maintenance and expression of GFP in human embryonic stem cells pp. 239-250; abstract.
Watson et al., Recombinant DNA, Second Edition, 2001 pp. 153-155.
Burton et al., Nature Immunology 2004 HIV vaccine design and the neutralizing antibody problem pp. 233-236.

(Continued)

*Primary Examiner* — Maria G Leavitt
(74) *Attorney, Agent, or Firm* — Boulware & Valoir; Meng-Tien Hsieh

(57) ABSTRACT

A composition of matter and method of treating HIV with mesenchymal stem cells (MSC) is disclosed. Specifically, MSCs are transduced with vectors incorporating an antiviral fusion inhibitor, such as a C46-derived peptide or neutralizing antibody. The transduced MSCs are capable of expression the inhibitor and preventing HIV virus-cell fusion.

2 Claims, 16 Drawing Sheets

(56) References Cited

OTHER PUBLICATIONS

Corti et al. 2013 Broadly Neutralizing Antiviral Antibodies Annu. Rev. Immunol. 2013. 31 :705-42.
Balyasnikova et al., Mesenchymal Stem Cells Modified with a Single-Chain Antibody against EGFRvIII Successfully Inhibit the Growth of Human Xenograph Malignant Glioma, PLoS ONE, www.plosone.org, Mar. 2010, vol. 5, Issue 3, e9750.
Bouma et al, Multiple Interactions across the Surface of the gp120 Core Structure Determine the Global Neutralizatior Resistance Phenotype of Human Immunodeficiency Virus Type 1 Journal of Virology, Jul. 2003, p. 8061-8071.
Chakrabarti et al., Direct Antibody Access to the HIV-1 Membrane-Proximal External Region Positively Correlates with Neutralization Sensitivity, Journal of Virology, Aug. 2011, p. 8217-8226.
Huang et al, Broad and potent neutralization of HIV-1 by a gp41-specific human antibody, Nature, vol. 491, Nov. 2012; pp. 406-411.
Lee, Narae; Drug delivery and homing function of mesenchymal stem cells in HIV therapy (2014) 117 pp. Avail ProQuest X LLC, Order No. AAI3703652 From: Diss Abstr. Int., B 2016, 76(9E), part 1 pp. 1-53.
Lee, Narae et al., The Potential Therapeutic Role of Secreted Antiviral Entry Inhibitory (SAVE) Peptides Expressed by Transduced MSCs to Block Viral Replication, Molecular Thereapy, vol. 21, Supplement 1, May 18, 2013.
Lee, Narae et al., Molecular Therapy, (Jun. 2014) vol. 22, Supp. 1, pp. S183. Abstract No. 476.
Poveda et al AIDS Rev. Jul.-Sep. 2005;7(3):139-47. Enfuvirtide, the first fusion inhibitor to treat HIV infection.
Zwick et al., Anti-Human Immunodeficiency Virus Type 1 (HIV-1) Antibodies 2F5 and 4E 10 Require Surprisingly Few Crucial Residues in the Membrane-Proximal External Region of Glycoprotein gp41 to Neutralize HIV-1 Journal of Virology, Jan. 2005,p. 1252-1261.
Tomchuck et al., Mesenchymal Stem Cells as a Novel Vaccine Platform, Frontiers in Cellular and Infection Microbiology, Nov. 2012, vol. 2, Article 140.
Balaz et al., Antibody Gene Transfer for HIV Immunoprophylaxis, Nature Immunology, vol. 14, No. 1, Jan. 2013.
Chen et al, Bifunctional Fusion Proteins of the Human Engineered Antibody Domain m36 with Human Soluble CD4 are Potent Inhibitors of Diverse HIV-1 Isolates, Antiviral Research 88, 107-115 (Oct. 1, 2010).
Lulu et al., A Bivalent Recombinant Protein Inactivates HIV-1 by Targeting the gp41 Prehairpin Fusion Intermediate Induced by CD4 D1D2 Domains, Retrovirology, 9:104 (Dec. 7, 2012).
Reiser Jakob et al., Potential of mesenchymal stem cells in gene therapy approaches for inherited and acquired diseases; Expert Opin. Biol. Ther., vol. 5, No. 12, Nov. 30, 2005, pp. 1571-1584.
Leavitt et al., J. Virol. Jan. 2003; 77(1):560-70, Concordant modulation of neutralization resistance and high infectivity of the primary human immunodeficiency virus type 1 MN strain and definition of a potential gp41 binding site in gp120. (Cited in Office Action in Parent Case Sep. 18, 2018).
Kay et al., Viral vectors for gene therapy: the art of turning infectious agents into vehicles of therapeutics, Nature Medicine, vol. 7, No. 1, Jan. 2001, pp. 330-340.
Addgene: Adenoviurs Guide pp. 1-3; downloaded Sep. 12, 2018.
Van Luzen, Jan, et al., Transfer of Autologous Gene-modified T Cells in HIV-infected Patients with Advanced Immunodeficiency and Drug-resistant Virus, Molecular Thereapy, vol. 15, No. 5, 1024-1033, May 2007.
Trobridge Protection of Stem Cell-Derived Lymphocytes in a Primate AIDS Gene Therapy Model after In Vivo Selection, PLoS One, vol. 4, Issue 11, e7693 (Nov. 2009).
Zahn, Efficient entry inhibition of human and nonhuman primate immunodeficiency virus by cell surface-expressed gp41-derived peptides, Gene Thereapy vol. 15, No. 17 1210-1222, May 2008.
International Search Report for EP counterpart, dated Jul. 20, 2016.

\* cited by examiner

1- HRST-CMV-eGFP (BamHI_(N6 mAb Heavy 22 + P2A + N6 mAb Light 22)_KpnI) plasmid
11,961 bp

EXPRESSION OF HIV INHIBITORS BY MESENCHYMAL STEM CELLS

PRIOR RELATED APPLICATIONS

This disclosure is a continuation-in-part of U.S. Ser. No. 14/782,115, filed Oct. 2, 2015 and abandoned on Mar. 19, 2018, which is a National Stage filing under 35 U.S.C. § 371 of International Application PCT/US14/32832, filed Apr. 3, 2014, which claims priority to U.S. Ser. No. 61/808,097, filed on Apr. 3, 2013. Each of these applications is expressly incorporated by reference in its entirety herein for all purposes.

FEDERALLY SPONSORED RESEARCH STATEMENT

Not applicable.

REFERENCE TO MICROFICHE APPENDIX

Not applicable.

FIELD OF THE DISCLOSURE

The present disclosure relates generally to methods of treating human immunodeficiency virus (HIV), and specifically, to the use of transduced mesenchymal stem cells to treat HIV.

BACKGROUND OF THE DISCLOSURE

Human immunodeficiency virus (HIV) is a slowly replicating retrovirus that leads to progressive failure of the immune system in humans, thus opening the door for life-threatening opportunistic infections and cancers to thrive. Infection with HIV results in CD4$^+$ T cells depletion through a number of mechanisms including: apoptosis of uninfected bystander cells; direct viral killing of infected cells; and, killing of infected CD4+ T cells by CD8 cytotoxic lymphocytes that recognize infected cells. The loss of the CD4$^+$ T cells causes Acquired Immune Deficiency Syndrome (AIDS). The loss of immune function from HIV and AIDS has led to the death of over 25 million people from AIDS worldwide.

Many therapies exist to manage but not cure HIV. Antiretroviral therapies (ART), for example, control viremia, a condition where viruses enter the bloodstream and have access to the rest of the body. The available anti-HIV drugs target different phases of the HIV life cycle, wherein each drug is classified according to the phase it inhibits. However, a standard ART consists of at least three antiretroviral drugs used in combination such that multiple phases of the HIV life cycle are inhibited and replication is suppressed as much as possible.

While showing promise in HIV and AIDS treatment, ART does have its drawbacks. Over 30 different types of drugs are available for ART, but only a few combinations may work for a given patient. A patient may have to cycle through multiple combinations and dosage levels before finding one that works. Multiple pills must be taken one or more times a day on a specific schedule to decrease a patient's viral load. Any deviation from the treatment schedule can result in mutations of the HIV/AIDS strain that may be resistant to the current drug combination. Furthermore, these medications may cause side effects, such as insulin resistance or lipid abnormalities, which also require additional medication in combination with the ART. Thus, the ART drug regimens are complex and expensive, requiring life-long intervention with potential side effects.

Like most viruses, HIV has a viral envelope. Embedded in HIV's viral envelope is a protein known as Env, which consists of a cap made of three molecules called glycoprotein (gp) 120, and a stem consisting of three gp41 molecules that anchor the virus structure into the viral envelope. Because this glycoprotein complex enables the virus to attach to and fuse with target cells to initiate infection, the glycoproteins are targeted by treatments and vaccines.

Enfuvirtide (fuzeon, or T-20) is an FDA-approved drug in a new class of fusion inhibitor that disrupts the HIV-1 molecular machinery at the final stage of fusion with the target cell. Enfuvirtide targets the gp41 glycoprotein during fusion. Specifically, gp41 undergoes conformational changes that allow fusion of HIV-1 to target cells. Enfuvirtide binds to gp41, thus preventing the creation of an entry pore for the virus, keeping it out of the cell.

However, this injectable drug has significant side effects and drug delivery issues as most patients develop some local injection site reaction. Furthermore, enfuvirtide has a short half-life, which requires twice daily administration, thus antagonizing the local injection site reaction. The subcutaneous application of enfuvirtide is also a distinct disadvantage in patients who are already burdened by complex oral therapy.

Thus, there exist a need for novel therapies that are less complex and more accommodating. Ideally, the new therapies will have limited side effects and a longer half-life.

SUMMARY OF THE DISCLOSURE

The present disclosure provides a novel composition of MSCs transduced with one or more retroviral and/or lentiviral vectors expressing anti-viral fusion inhibitors of the HIV infection and methods of use. In accordance with this discovery, the disclosure also provides a method of inhibiting HIV infection using transduced MSC expressing these inhibitors.

Multipotent stem cells, such as mesenchymal stem cells (MSCs), are stem cells capable of differentiating into cells specific to tissues and organs containing these cells and are involved in fetal, neonatal and adult periods of growth and development, but also in the maintenance of homeostasis of adult tissue and the functioning of inducing regeneration upon tissue damage. The variety of cell types that MSCs can differentiate into is illustrated in FIG. 1.

MSCs have been proposed for the treatment of numerous illnesses in part because these cells have been shown to migrate to sites of inflammation and tumors. Unlike most other human adult stem cells, MSC can be obtained in quantities appropriate for clinical applications, making them good candidates for use in tissue repair. Furthermore, they also have antiproliferative, immunomodulatory and anti-inflammatory effects and are low immunogenic. Although the mechanism underlying the immunosuppressive effects of MSCs has not been clearly defined, their immunosuppressive properties have already been exploited in the clinical setting. Therefore, MSCs have implications for treatment of allograft rejection, graft-versus-host disease, rheumatoid arthritis, autoimmune inflammatory bowel disease and other disorders in which immunomodulation and tissue repair are required.

In addition to tissue repair, MSCs have also been used in certain virus treatments. WO2010053350 describes the use of MSCs for inhibition of a hepatitis viral infection. Here, cells replicating the virus are contacted with either a liquid containing MSCs or with an exudate of the MSCs. However, MSCs have never been shown to migrate to virus-infective cells or to express inhibitors of viruses such as HIV.

In the present disclosure, it was determined that MSCs can be used as "trojan bioreactors" to carry and express a variety of HIV inhibitors at local sites of infection and virus-infective cells. The MSCs were transduced with retroviral and lentiviral vectors packaged with antiviral fusion inhibitors of the HIV infection. The transduced MSCs were able to express the inhibitors and maintain differentiation abilities. In addition to inhibiting HIV fusion, these transduced MSC are expected to reduce the general immune activation frequently observed in patients with HIV infection as has been shown by MSC treatment in other disease indications. Other vectors such as Adeno-associated virus can also be used.

In one embodiment, the present disclosure provides transduced MSCs expressing certain inhibitors to treat HIV. Specifically, HIV anti-viral fusion inhibitors are incorporated into delivery vehicles such as retroviruses and lentiviruses. These delivery vehicles are introduced into the MSCs, wherein the cells under go transduction. The transduced MSC are then able to express the HIV peptide inhibitors while retaining important characteristics such as the capacity for osteogenic, adipogenic, and chondrogenic differentiation.

In another embodiment, a method of treating human immunodeficiency virus by administering mesenchymal stems cells expressing anti-viral fusion inhibitors of HIV infection is disclosed. The MSCs will provide long-term, continuous expression of the inhibitors without the side effects associated with currently available injectable HIV inhibitors, such as injection-site irritation and difficulties in handling.

In another embodiment, the present disclosure provides a method of inhibiting HIV infection by administering conditioned medium from transduced MSC expressing anti-viral fusion inhibitors.

Additionally, the above methods can be combined with an anti-HIV drug treatment. The MSCs can be administered before, during or after the antiviral drugs are administered. Preferably, the MSCs are administered after the antiviral drugs.

In some embodiments, the transduced MSCs are administered directly to a subject. In other embodiments, the MSCs or conditioned media is mixed with an appropriate pharmaceutical carrier for administration. Preferred routes of administration are intravenous, subcutaneous and intraperitoneal injections.

Multiple HIV anti-viral fusion inhibitors can be used with the present composition and methods. Peptide inhibitors that block different points in the HIV replication and fusion mechanism by targeting CCR5, CD4-binding, gp41 and envelope can be used in the above embodiments. As can fusion proteins or soluble CD4 molecules. In addition to, or in place of, peptide inhibitors, neutralizing antibodies can be packaged into the vectors. Neutralizing antibodies defend a cell from an antigen or infectious body by inhibiting or neutralizing any effect it has biologically.

Exemplary peptide inhibitors are C46 peptides, which are derived from the HR2 gene of gp41. Secretable antiviral entry inhibitory (SAVE) peptides for C46 such as those in US20110027240, which is incorporated herein in its entirety, can also be used. For instance, a customized C46 peptide:

WMEWDREINNYTSLIHSLIEESQNQQEKNEQEL-LELDKWASLWNWF (SEQ NO. 1) was used in some embodiments of the present disclosed methods. T-20: YTS-LIHSLIEESQNQQEKNEQELLELDKWASLWNWF (SEQ No. 2), provided through the NIH AIDS Reagent Program, division of AIDS, NIAID, NIH: T-20, fusion Inhibitor from AIDS, NIAID, is another possible peptide inhibitor. Such SAVE peptides are known to disrupt the fusion mechanism by blocking the gp41 viral envelope protein. Other peptide inhibitors of HIV replication, in addition to the C46 SAVE peptides, would be acceptable in the presently disclosed composition and method.

Exemplary antibody inhibitors include polyclonal, monoclonal, humanized, anti-idiotypic, chimeric or single chain antibody inhibitors. Preferably, the antibody inhibitors are single-chain neutralizing antibodies inhibitors such as B404, N6, 10E8v4, and/or 35022, or neutralizing monoclonal antibodies. In some embodiments, one or more neutralizing antibodies are used together. In other embodiments, both neutralizing antibodies and fusion proteins, protein inhibitors, and/or soluble CD4 molecules are used together for treatment.

The sequence of the peptide or antibody inhibitors are incorporated into retroviral, lentiviral and/or Adeno-associated virus (AVV) vectors before being transduced in the MSCs. Success of the transduction is confirmed by analyzing the MSCs using commonly acceptable practices to confirm expression of the peptide or antibody inhibitors. Once expression is confirmed, the MSCs can be injected into a person who has HIV, who has been exposed to HIV, or who is at risk for exposure to HIV.

The inhibitors can be packaged into the retroviral and lentiviral vectors using any known method in the art, typically, using purchased kits. Invitrogen offers lentiviral packaging kits, as does InvivoGen. The National Gene Vector Biodepository has both retroviral and lentiviral vectors that are suitable for human clinical studies and publically available. Additionally, markers such as green fluorescence protein can also be packaged to facilitate confirmation of expression and determine transduction efficiency.

The MSCs for the present methods can be allogeneic or autologous, depending on the stage of infection and degree of immune deficiency. All acceptable methods of extraction of MSC can be used in the present methods. Preferably, MSCs derived from adipose tissue are utilized due to the large number of cells per volume of sample. Furthermore, adipose tissue is much easier to access than other sources such as bone marrow, which is particularly important for immune-compromised subjects. However, because MSCs can be expanded in culture before being transduced, other sources of MSCs, such as bone marrow, can be utilized.

The described composition and treatment methods can be applied to animals, preferably mammals, and most preferably, to humans.

In the context of the disclosure, "HIV" includes HIV-1 and HIV-2 types. Further included are all natural HIV strains (quasi-species or isolates). In this respect, it is understood that HIV strains include all known HIV strains as listed in the Los Alamos National Laboratory HIV Sequence Database.

As used herein, "mesenchymal stem cells" means any cells that meet the criteria set forth by The Mesenchymal and Tissue Stem Cell Committee of the International Society for Cellular Therapy (ISCT). Under this criteria, MSCs: 1) are plastic-adherent when maintained under standard culture conditions (especially in the presence of human or fetal bovine serum); 2) have the capacity for osteogenic, adipogenic, and chondrogenic differentiation; 3) express CD73, CD90, and CD105; and 4) lack expression of the hematopoietic lineage markers c-kit, CD14, CD11b, CD34, CD45, CD19, CD79, and human leukocyte antigen-DR.

The term "autologous" as used herein shall be taken to mean from the same individual.

The term "allogeneic" as used herein shall be taken to mean from an individual separate from the individual being treated.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the disclosure.

The following abbreviations are used herein:

| ABBREVIATION | TERM |
|---|---|
| ART | Antiretroviral therapies |
| BMS | Bone marrow MSCs |
| CM | Conditioned media |
| FACs | Fluorescence-activated cell sorting |
| GFP | Green fluorescent protein |
| HIV | Human immunodeficiency virus |
| MSC | Mesenchymal Stem Cells |
| NAB | Neutralizing antibody |
| Rh | Rhesus |

BRIEF DESCRIPTION OF THE DRAWINGS

FIG. 11A shows an expression vector encoding the light chain of the N6 mAb; FIG. 11B shows an expression vector encoding the heavy chain of the N6 mAb;

FIG. 11C shows a lentiviral vector encoding both the light and heavy chains of the N6 mAb with a P2A self-cleaving element to separate the heavy and light chains after expression.

FIG. 12 displays varying concentrations (10%, 25%, and 50%) of conditioned media expressing B404 against SIV to inhibit viral infection of TZM-bl reporter cells.

FIG. 13 displays varying concentrations (10%, 25%, and 50%) of conditioned media expressing N6, 10E8v4, and/or 35022 against HIV-BaL to inhibit viral infection of TZM-bl reporter cells.

DETAILED DESCRIPTION

The disclosure describes novel transduced mesenchymal stems cells (MSC) that express HIV virus-cell fusion inhibitors and a method of use to treat HIV. Specifically, mesenchymal stems cells (MSC) are transduced with one or more retroviral and/or lentiviral vectors expressing antiviral fusion inhibitors of HIV is disclosed. The transduced MSCs express the inhibitors without losing important MSC characteristics such as the ability to differentiate.

Methods of using the novel composition can comprise treating an animal, and preferably a human, suffering from an HIV infection wherein a peptide inhibitor or neutralizing antibody is incorporated into a viral or nonviral vector, which is then transduced into a MSC such that the MSC can express the inhibitor. The transduced MSCs are then administered to a subject alone or in combination with antiretroviral therapies. The MSCs can be autologous or allogenic and taken from any source including bone marrow or adipose tissue. Preferred viral vectors are lentivirus, retrovirus, or any combination thereof. Exemplary inhibitors include one or more of secreted antiviral entry inhibitory (SAVE) peptides, C46, maC46 or neutralizing antibodies. The MSCs can be administered intravenously, subcutaneously, or intraperitonealy.

FIG. 2 displays the fusion mechanism by which HIV infects new cells. HIV fusion with a target cell starts with the attachment of gp120 to the N-terminal domain of the CD4+ receptors (B) Once attached, gp120 undergoes a conformational change that unmasks the binding site for the cell co-receptor (C). Once the virus is bound, a conformational change exposes the N-terminal hydrophobic region of gp41 to the CD4+ cell membrane and becomes the "pre-hairpin intermediate". Gp41 undergoes a conformation change (D), also referred to as a coiled-coil bundle, to bring the virus and cell membranes together, mediating fusion of virus and cell (E).

In one aspect of the present disclosure, to inhibit the fusion of HIV, MSCs are transduced with HIV peptide inhibitors. Many HIV peptide inhibitors exist including maC46 and C46 peptides. The HIV entry inhibitor maC46 is a membrane-anchored peptide derived from the second heptad repeat of the HIV-1 transmembrane glycoprotein gp41. C46 peptides are members of the new fusion inhibitor class of antiretroviral drugs that efficiently block infection of new cells by interfering with the function of gp41. The C46 peptides can be membrane-bound or secreted.

The peptide inhibitors are incorporated into retroviral or lentiviral vectors, which act as gene delivery vehicles for transducing the MSCs with the peptide inhibitors. Exemplary vectors include murine leukemia (MLV) and self-inactivating lentiviral vectors (HSRT), however other viral or non-viral vectors systems would also be applicable. FIG. 3 displays a few of the virus vectors that have incorporated the peptide inhibitors, particularly the maC46 and SAVE peptide sequences. The vectors can also contain a fluorescence marker, such as GFP, to aid in monitoring the success of the transduction.

Similarly to the peptide inhibitors, MSCs can be transduced with HIV antibody inhibitors to inhibit the fusion of HIV. Many HIV antibody inhibitors, also referred to as antiviral fusion inhibiting antibody herein, exist, including neutralizing antibodies. Broadly neutralizing antibodies (bNAbs), for example, can be used to target HIV epitopes, thus neutralizing multiple HIV strains, even if the virus mutates.

After being transduced, the MSC can be analyzed to confirm expression of the peptide inhibitors using fluorescent microscopy, PCR, differentiation assays and other commonly used techniques.

The present disclosure is exemplified with respect to the examples and figures below. However, this is exemplary only, and the disclosure can be broadly applied to incorporate any HIV fusion inhibitor for all phases of the HIV life cycle and can be used for any animal. The following experiments and examples are intended to be illustrative only, and not unduly limit the scope of the appended claims.

Example 1

The overall idea of the presently disclosed method is to use MSCs with modified genomes as a 'Trojan horse' bioreactor to treat HIV. MSCs are known to migrate to sites of infection and tumors. However, MSCs have never been shown to migrate to virus-infective cells. Such migration is of particular importance for the presently disclosed methods, as the MSCs will be used to carry and express a large variety of HIV inhibitors at the sites of virus-infected cells.

Figure 4A:
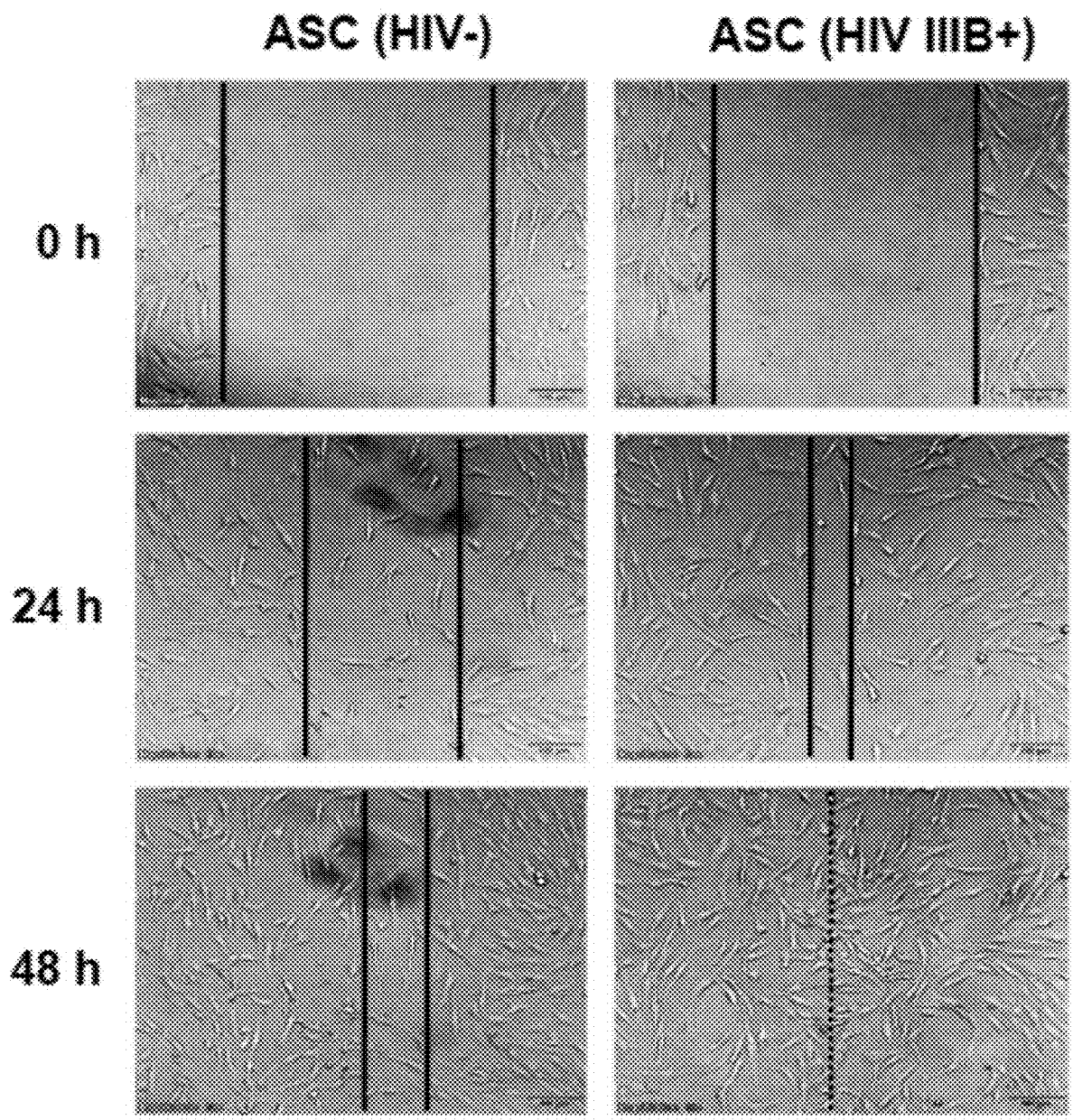
FIG. 4A shows the motility of MSCs in the presence of HIV-1 infection and FIG. 4B-C shows the migration of MSCs to towards e.g. HIV-1 released from chronically infected lymphocytes (ACH2 cells).
Figure 4B:
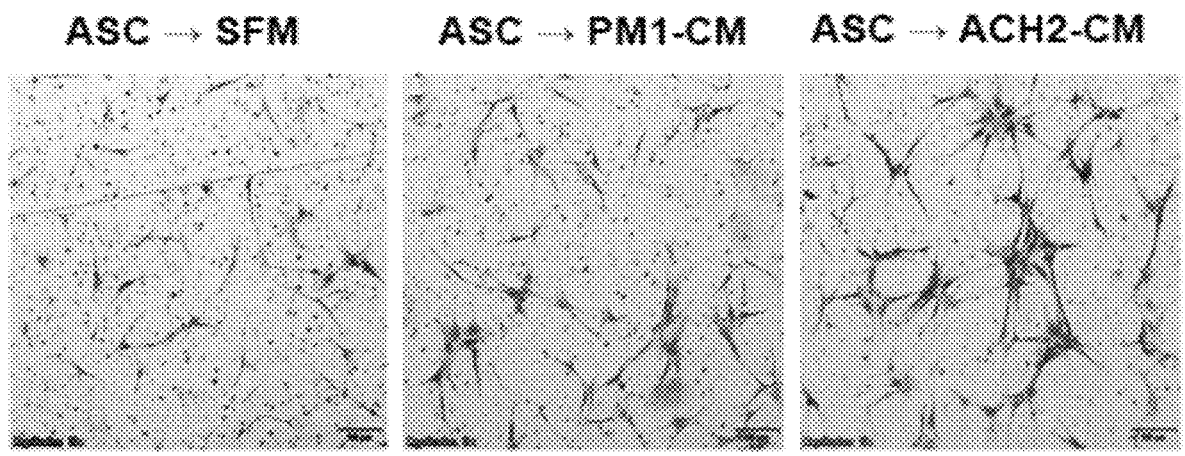
Figure 4C:
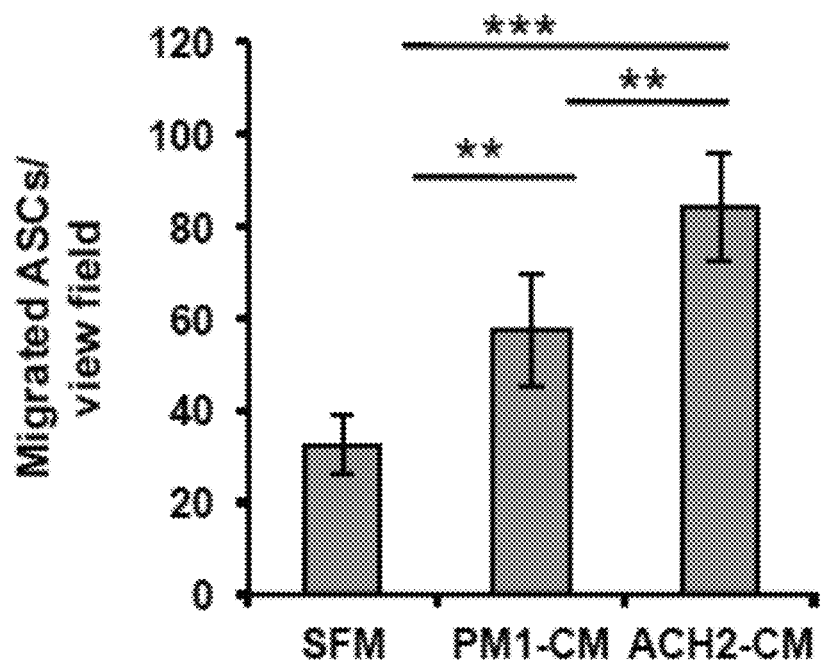
Figure 5:
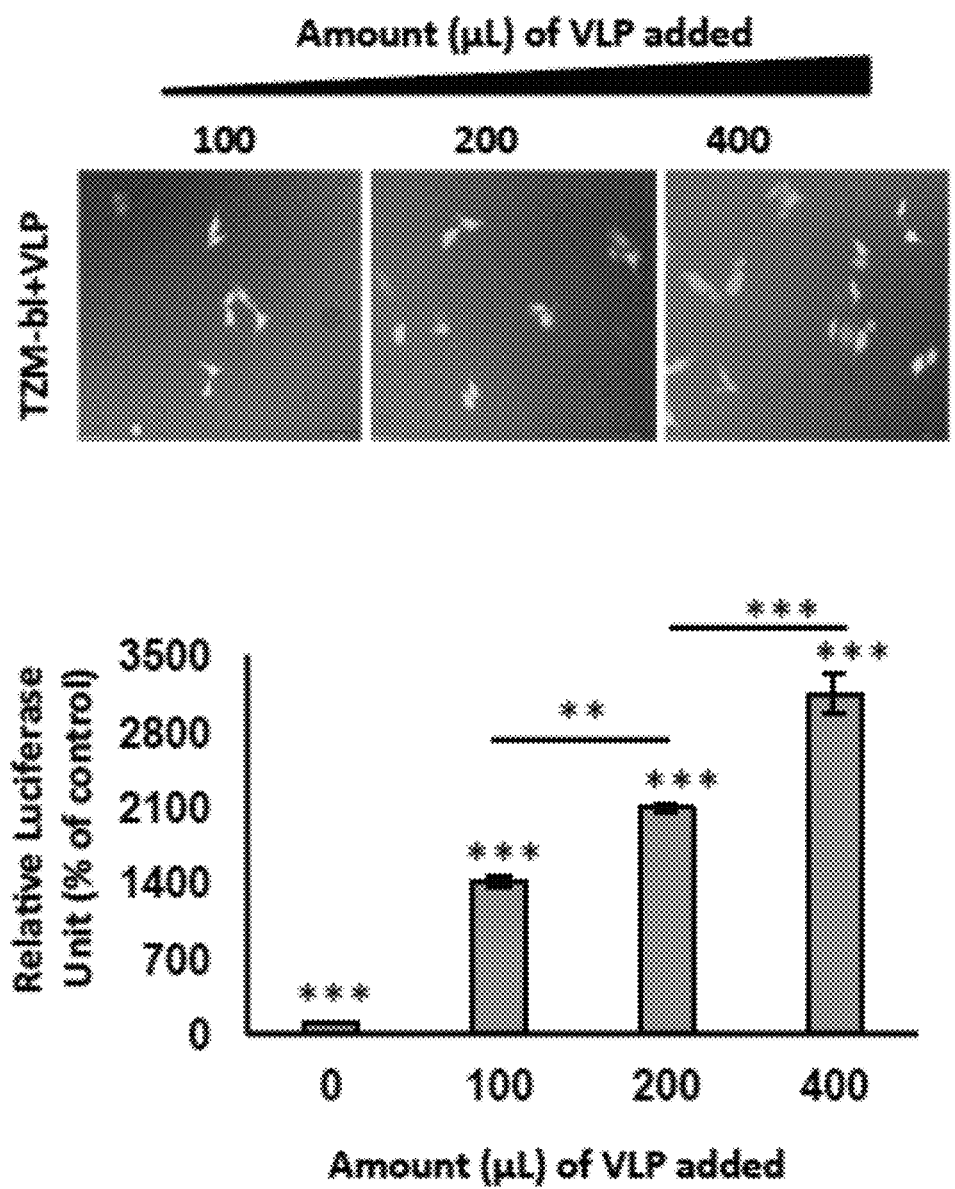
FIG. 5. shows evidence that the MSCs inhibit HIV-1 infection and replication.

For the first time, evidence of MSC migration to local, virus-infective sites is being show. FIG. 4A shows the motility of MSCs in the presence of an HIV-1 infection. As seen in FIG. 4B-C, the MSCs migrate towards HIV-1 released from chronically infected lymphocytes (ACH2 cells). In FIG. 5, the MSCs are inhibiting the HIV-1 infection and replication process.

Results:

MSCs have been proven to be capable of migrating to cells infected with a virus. However, long term, continuous expression of inhibitors is desired as a proper treatment method for the virus. Thus, MSCs that can continuously express multiple inhibitors to treat HIV viruses, regardless of the location of the infected cells, are a desirable treatment method.

Example 2

Gene transfer and expression was performed by the following steps:

Cells:

Human Bone Marrow stem cells (HuMSCs), Rhesus Bone Marrow Stem cells (RhMSCs), and Rhesus Adipose stem cells (RhACSs) were plated at 10,000/cm² in alpha-MEM/20% FBS with no antibiotics the day before transduction.

Figure 1:
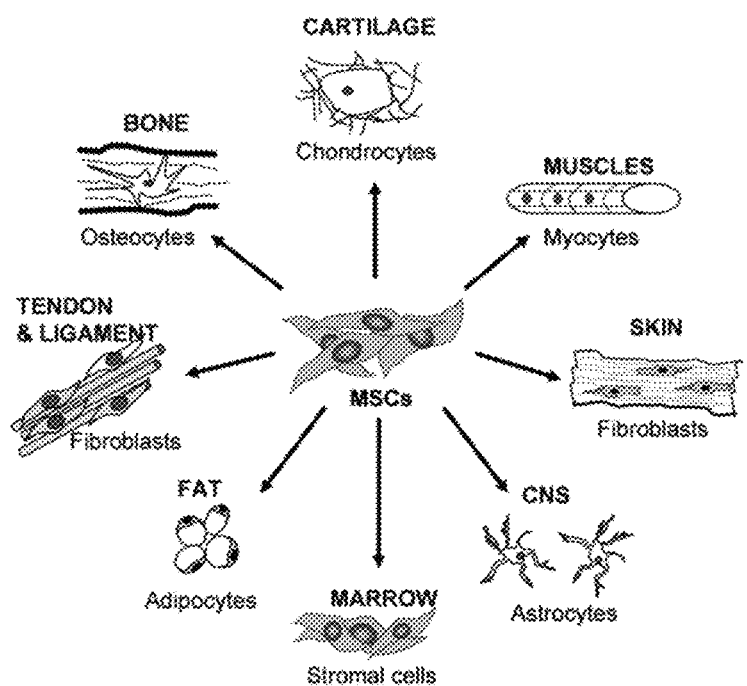
FIG. 1. Illustration of potential cell types upon MSC differentiation.
Figure 2:
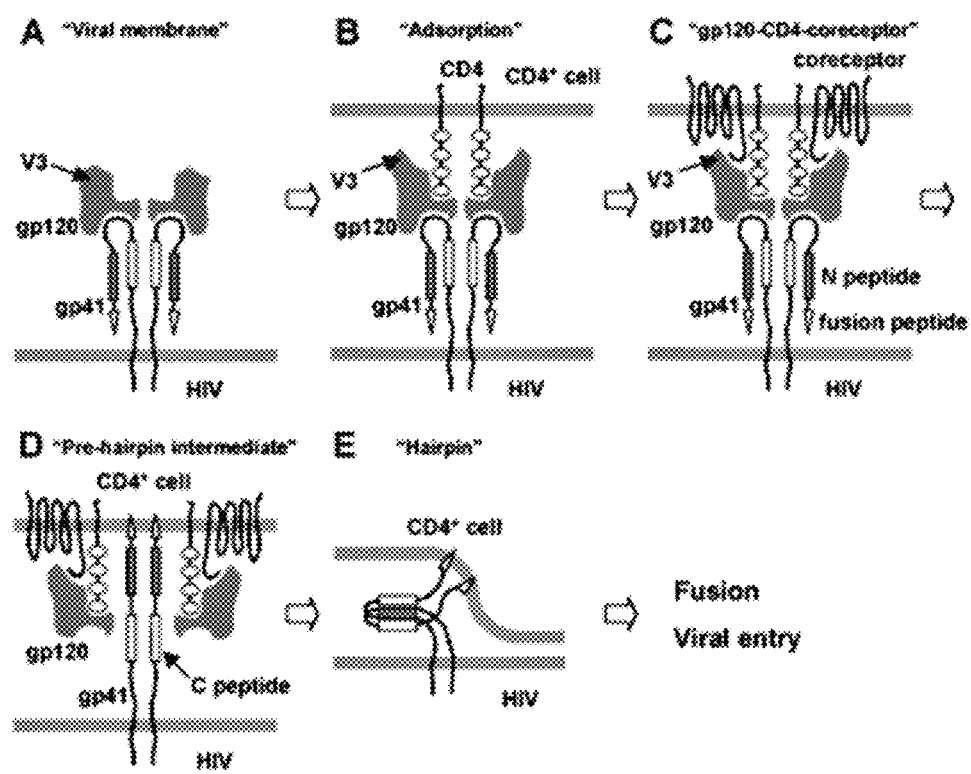
FIG. 2 shows a diagram of the HIV fusion mechanism. From *Drugs Fut.* 1999, 24(12): 1355.
Figure 3:
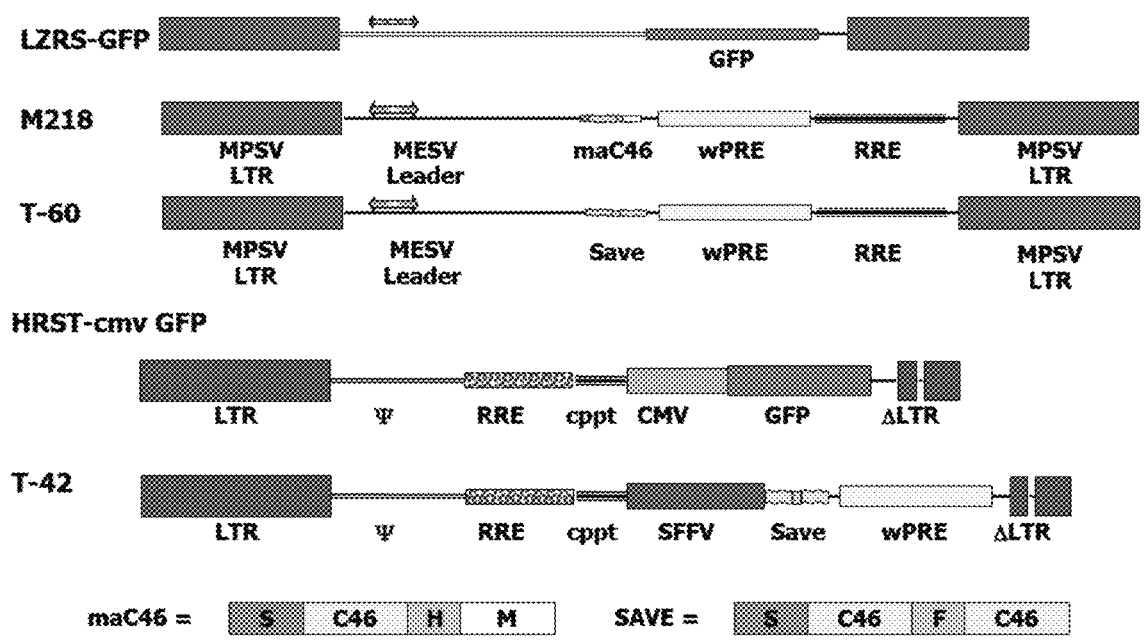
FIG. 3 shows the design of a number of vectors.

For transduction, the plated cells were exposed to various MOI of the control vectors, such as LZRS-GFP (19) or HRST-cmvGFP (38), or the therapeutic vectors, such as T42 (unknown), T60 (22), and M218 (unknown), containing the C46 peptide sequences shown in FIG. 3. Then, the plates were centrifuged at 1000 rpm for 1-2 hours. After which, the MSCs were cultured at 37° C. and 5% $CO_2$ for two days. After Day 2, cells were returned to standard culture conditions, wherein the cells were re-suspended in complete conditioned media and filter through a 70 mm cell strainer.

Expression Confirmation:

Fluorescent microscopy and flow cytometry were used to assess the expression of the C46 peptide using GFP. Real time PCR was also performed.

Figure 6:
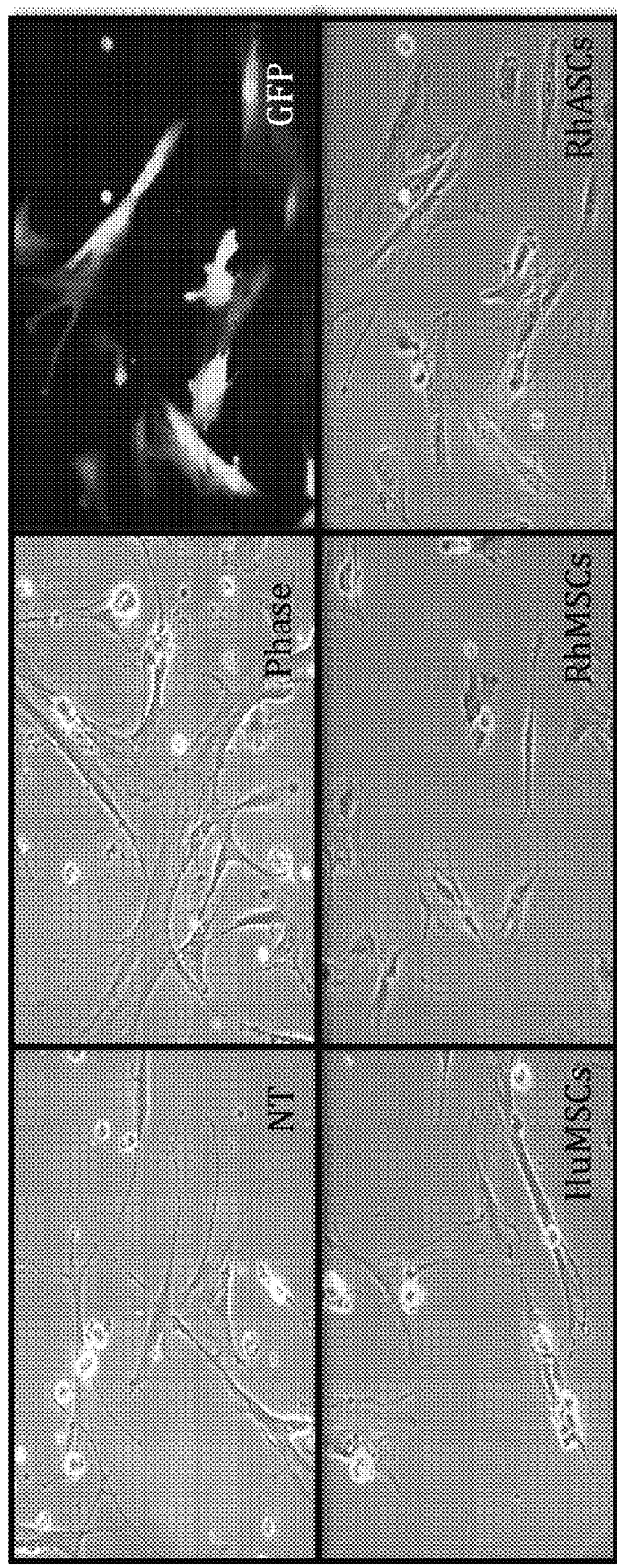
FIG. 6 shows a determination of transduction level using GFP+ cells.

As shown in FIG. 6, cells were observed under fluorescent microscope to confirm transduction and expression of GFP in transduced cells. The upper panels are, from left, non-transduced (NT) MSC, rhASC with phase contrast, and GFP expression overlayed onto the phase contract image. Lower panels show overlay of GFP expression in HuMSCs, RhMSCs, and RhACSs transduced with HRST-cmvGFP. As seen, the GFP is readily expressed in the human and rhesus stem cells.

Figure 7:
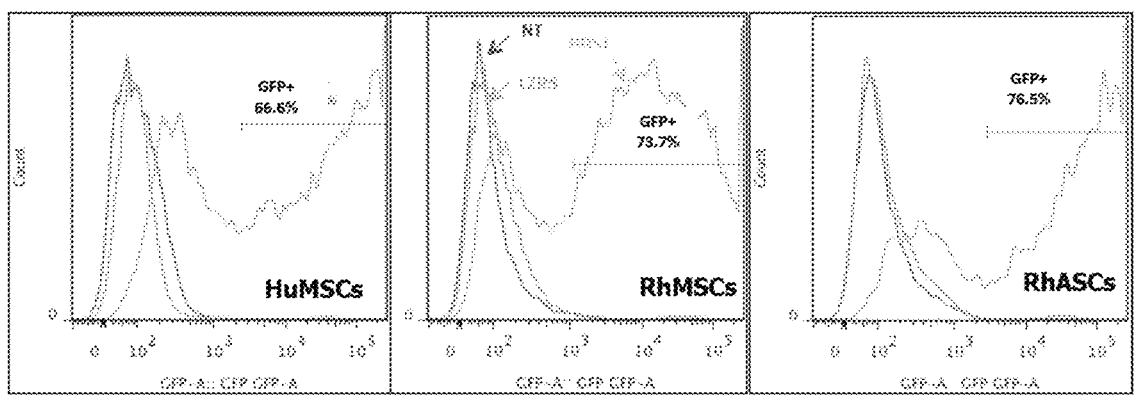
FIG. 7 shows GFP+ levels by flow cytometry.

FIG. 7 displays the flow cytometry Fluorescence-activated cell sorting (FACs) results for HuMSCs, RhMSCs, and RhACSs. For this analysis, cells were trypsinized and washed with 1% mouse serum. After the wash, cells were fixed with 4% paraformaldehyde and analyzed for GFP expression by flow cytometry. The NT control population was set as background fluorescence.

The HRST-GFP showed the highest expression levels in all three populations by FACs analysis. The LZRS-transduced MSC showed slightly elevated levels of GFP expression in all three MSCs populations.

Gene transfer and expression was detectable up to 69% in MSCs by fluorescent microcopy and flow cytometry.

The real time PCR results for the vector backbone, shown below, detected between 5-25% of the human MSCs, rhesus MSCs, and HEK 293 cells contained the Psi packaging element in T60 and M218. Both T60 and M218 are murine leukemia virus based vectors.

| | C46 Vector | |
| --- | --- | --- |
| Cell type | T60 (%) | M218 (%) |
| Hu MSC | 3.9 | 6.3 |
| Rh MSC | 12.5 | 25.5 |
| Rhs ASC | 10.6 | 14.7 |
| 293T | 10.0 | 13.3 |

Figure 8:
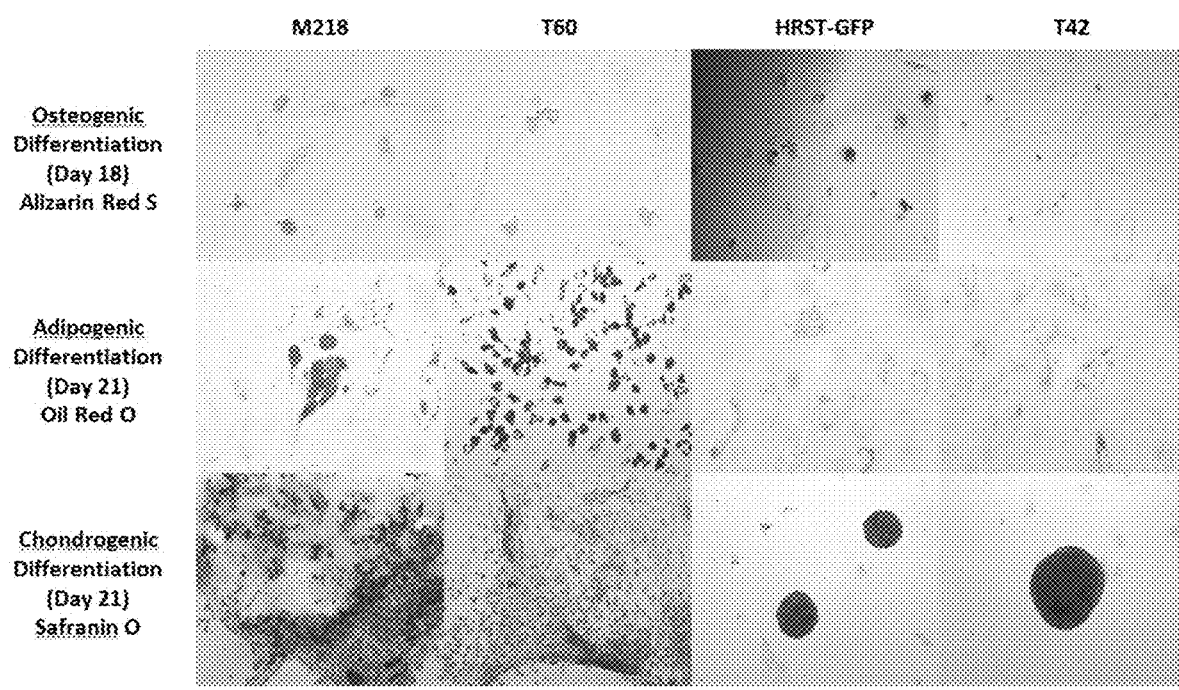
FIG. 8 shows confirmation of a transduced RhBMS Differentiation Assay.

Differention assays were also performed to confirm transduced RhMSCs to test that the inhibitors do not disturb MSCs differentiation and results are shown in FIG. 8. The osteogenic, adipogenic, and chrondrogenic differentiation abilities of the MSCs were taken at 21 days for the M218, T60, HRST-GFP and T42 vector. As seen in FIG. 8, the MSCs retained their ability to differentiate into multiple cells, regardless of the vector or peptide inhibitor used. This shows that MSCs have not lost their differentiation abilities after being transduced.

Results:

The HIV1-based lentiviral vector HRST-cmvGFP was superior to LZRS-GFP in both the frequency of gene transfer and the level of expression. Furthermore, real-time PCR data showed a transduction rate of 5-25% in the MSCs for MLV C46 vectors.

Example 3

The above method in Example 2 was applied to a larger variety of cells.

Cells:

Most cells were obtained from the NIH AIDS Reagent Program. The NIH AIDS Reagent Program is a worldwide resource for state-of the art HIV research materials, some of which are not yet commercially available. CEM×174 cells (NIH AIDS Reagent Program Cat no. 272), expressing CD4, T and B cell markers, were obtained because they are easily infected with HIV virus. Second T-cell line "PM-1" (NIH AIDS Reagent Program Cat no. 3038), permissive for growth of macrophage and T cell tropic viruses, a subclone of HuT78 (Human T cell lymphoma) expressing CD4, CXCR4, and CCR5, was obtained. All T-cell lines were cultured in Roswell Park Memorial Institute medium (RPMI) 1640 medium.

Human TZM-bl cell (NIH AIDS Reagent Program Cat no. 8129), previously designated JC53-bl (clone 13) is a HeLa cell line. The parental cell line (JC.53) stably expresses large amounts of CD4 and CCR5. The TZM-bl cell line was generated from JC.53 cells by introducing separate integrated copies of the luciferase and ß-galactosidase genes under control of the HIV-1 promoter. All media were supplemented with 10% fetal bovine serum, 4 mM L-glutamine, 10,000 U/mL penicillin/streptomycin.

Rhesus macaque bone marrow/adipocyte derived mesenchymal stem cells were isolated and maintained in complete culture medium, 20% FBS MEM α (Minimum Essential Medium α), with 1-glutamine, fetal bovine serum (Atlanta Biologicals Premium Select FBS), Penicillin G (10,000 units/mL), and streptomycin sulfate (10,000 µg/mL) in solution of 0.85% NaCl (Invitrogen/GIBCO).

Human embryonic kidney cell line 293T was obtained from the ATCC, and was maintained in Dulbecco's modified Eagle's medium (DMEM).

Bone Marrow and Adipose Derived Mesenchymal Stem Cells Isolation and Culture:

Bone marrow-derived mesenchymal stem cells were isolated by discontinuous density gradient centrifugation following the Tulane Center for Stem Cell Research and Regenerative Medicine protocol. Briefly, LSM (Lymphocyte Separation Medium, ICN50494, MP Biomedicals, No.: 0850494) one-step separation medium was underlayered beneath the bone marrow mixture. The sample was centrifuged at 1400 rpm (~400 g) for 40 min. The low-density mononuclear cells were collect at the white interface and washed with fresh media. After the last centrifugation, the supernatant discard and a lysis buffer (ACK lysing buffer, Gibco, catalog no. 10492-01) was used to eliminate residual red blood cells.

The collected cells were plated at a concentration of ~1-2 million cells in a 15 cm tissue culture dish and incubate at 37° C. in 5% $CO_2$. The complete culture medium was changed the next day (24 hours later) and replace with fresh complete medium. When the plate was about 70-80% confluent (~14 days), cells were trypsinized and frozen at P0 in Liquid $N_2$ until they were expand to P1 or frozen as a pellet for DNA and protein analysis.

Adipose-derived stem cells were isolated according to the Tulane Center for Stem Cell Research and Regenerative Medicine protocol. Briefly, the adipose tissue was washed extensively with a 5% Phosphate Buffer Solution (PBS 5% p/s) before being minced into small pieces using a sterile scalpel. The pieces were placed in a 15 cm dish with 0.075% Collagenase Type I (Gibco, catalog no. 17100-017) in PBS. Collagenased tissues were incubated for 30 min at 37° C. at 5% $CO_2$. The liquid portion was removed and the plate was washed several times with PBS 2% p/s, and centrifuge to obtain a pellet. After lysing with ACK Lysing Buffer (Gibco, catalog no. 10492-01), the adipose-derived cells were washed and incubated for 10 min on ice to lyse any red cells. The cells were again washed with 20 ml PBS 2% p/s, wherein the supernatant was discard. The cell pellets were re-suspended in complete conditioned media and filter through a 70 mm cell strainer.

Collected cells were plated into the proper size culture dish depending on the size of cell pellet and incubate at 37° C. at 5% $CO_2$. The media was changed the next day and replaced with fresh media. When the plate was about 70-80% confluent, aspirate the medium. Cells were frozen and stored in liquid $N_2$ until they used to expand to P1, and then were frozen a pellet for DNA and protein analysis.

Peptide Cloning and Mesenchymal Stem Cells Transduction:

The C46 peptide used in the present experiment was SEQ No. 1.

C46 peptides driven by Murine leukemia virus (MLV) and lentivirus (M218, T60, and T42) and control vectors (LZRS-GFP and HRST-cmv-GFP) were transformed using one shot stb13 kit with competent cells (Invitrogen, Cat. No. C7373-03) followed by manufacture's procedure. After sitting overnight, the colonies were selected and a single colony was grown in LB medium plus ampicillin overnight. DNA mini prep was performed with PureLink® Genomic DNA Mini Kit (Invitrogen, Catalog No. 1820-01).

Transient transduction of 293T cells with MLV and lentiviral vectors were completed by the calcium phosphate precipitation method. The calcium phosphate transduction method is used for introducing DNA into mammalian cells and is based on forming a calcium phosphate-DNA precipitate. Calcium phosphate facilitates the binding of the DNA to the cell surface. DNA then enters the cell by endocytosis.

15 µg of MLV vector plasmid was used for LZRS-GFP and LZRS-T60 and 2 ug of LZRS-M218 was used for transfection of the Phoenix (amphotropic) packaging cell line, a cell line bases on HEK 293T cells. They constitutively express the MLV Gag/Pol and amphotropic envelope genes. Addition of the vector genome will generate replication defective MLV-based retroviral particles in the supernatant. For the HIV-based lentiviral vectors, 13 ug of HRST-GFP or T42 vector DNA was transfected along with the HIV packaging plasmids [pHDM-Hgm2 (gag/pol), pRC/Rev, pHDM-Tat 1b, envelope HIV-1 JRFL or VSV-G (pHDM.G)] or packaging vector (M438).

Cell culture supernatants containing replication defective lentiviral particles were collected from 24 to 48 hours post-transduction, filtered (0.22 µm pore size) and stored at −80° C. until use.

Transduction of Mesenchymal Stem Cells with Lentiviral and MLV Vectors:

$1 \times 10^5$ cells/well of MSCs were plated in 6 well-plate a day before transduction. A desired amount of viral supernatant was added into each well, such as 1 ml of non-concentrated viral supernatant or 100 ul of concentrated viral supernatant. MSCs were transduced with MLV vector and lentiviral vector supernatants by spinoculation (1 hr, 1200 rpm, 31° C.) then incubated at 37° C. in 5% $CO_2$.

At day 2, the viral supernatant was removed and fresh 20% FBS alpha-MEM with no antibiotics was added to the MSCs. This media was change with 20% FBS alpha-MEM with no antibiotics at day 4. At day 6-7, depending on cell density, cells were prepared for fluorescent microscopy, flow cytometry, and quantitative proviral integrations by real-time PCR. Transduction efficacies were determined 3 days after transduction by flow cytometry.

Figure 9A:
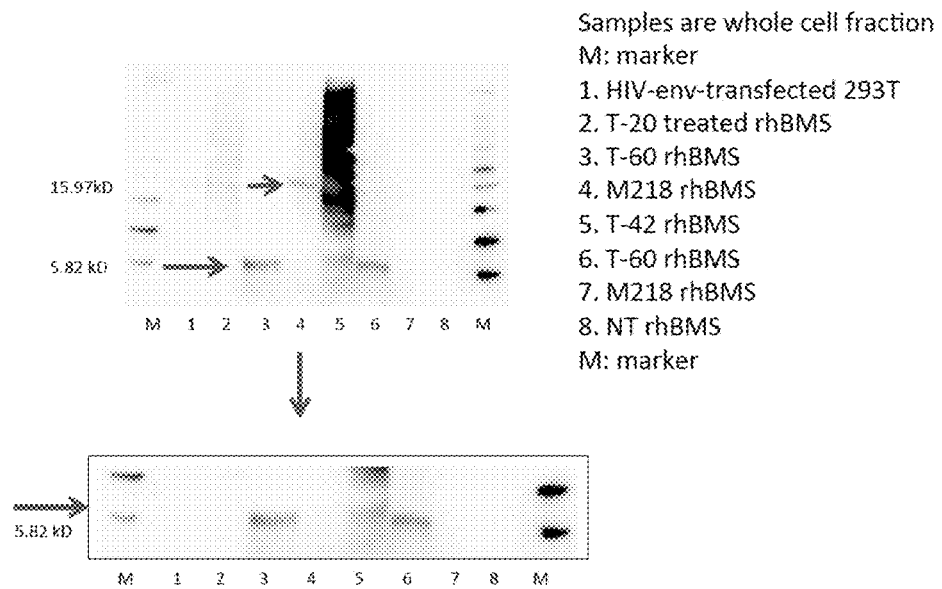
FIG. 9A-B display western blots of MSCs transduced with various HIV peptide inhibitors packaged in virus vectors, wherein RhBMS cells are in 7A and 293T cells are in 7B.
Figure 9B:
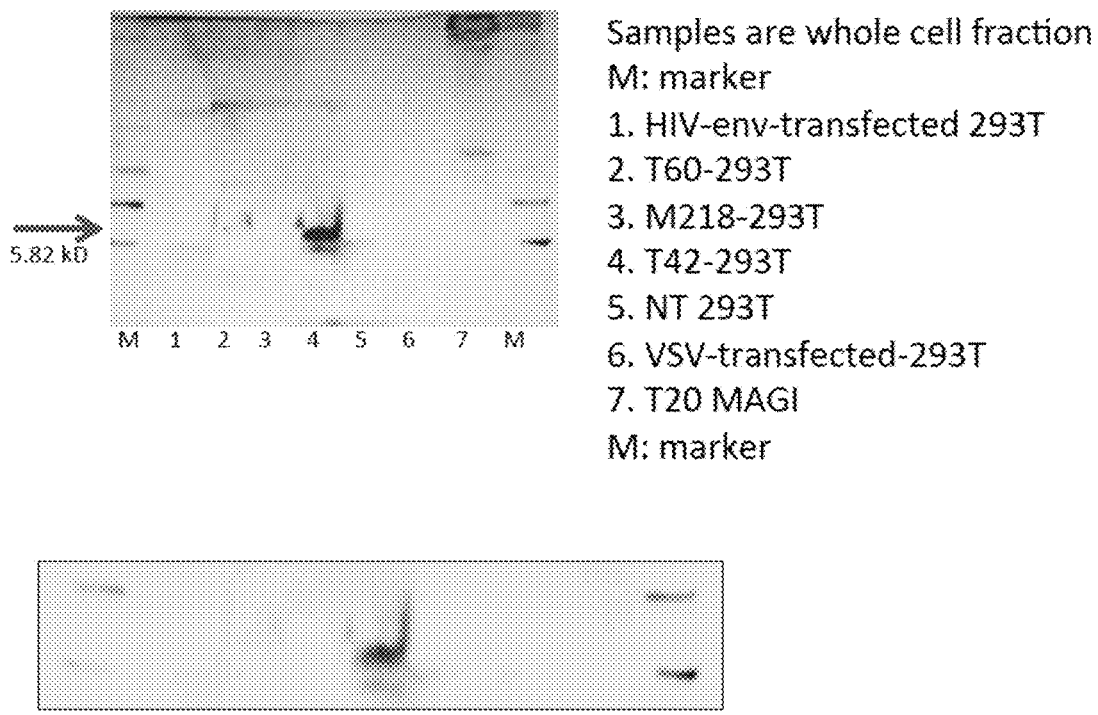

Detection of Secreted Version of C Peptides:

To determine the secreted C46 peptides in mesenchymal cell culture supernatants and cell lysates, a western blot analysis was performed and is shown in FIGS. 9A and B. Human HIV-1 gp41 monoclonal antibody (2F5) was obtained from the NIH AIDS Reagent Program. 2F5 allowed the binding of the antibody to all available C peptides.

The secreted peptides were apparent at the 5.82 kD level. This shows that the peptide inhibitors are being secreted by the MSCs and can be available for HIV treatments.

Preparation of HIV Pseudotyped Particles:

Day before transduction, $9 \times 10^6$ cells of 293T cells were plated on 15 cm culture dish for a total of 10 plates. Additional plates were prepared for VSV-G control. 80% of confluency was confirmed under microscopy on the day of transduction.

For the transient transfection, HRST-GFP was mixed with pHDM-Hgm2 (gag/pol), pRC/Rev, pHDM-Tat 1b, and envelope gene (either HIV-1 JRFL envelope or the VSV-G control envelope, pHDM.G). All the listed plasmid vectors were gift from Dr. Richard C. Mulligan, Harvard Gene Therapy Institute except JRFL envelope plasmid was provided by Dr. Dorothee von Laer from Innsbruck Medical University. 2.5M $CaCl_2$ and 2×HBS solution was added equal ratio. Final volume of 1 ml of transduction mixture was applied into each culture dish. After 6 hours later, fresh 10% DMEM medium was replaced. Viral supernatant was collected 24-48 hrs after transduction and filtered through 0.22 um size and treated with 5×PEG-it virus precipitation solution (PEG-It™ Virus Precipitation Solution (5×), SBI, Cat. #LV810A-1/LV825A-1) for 48-72 hrs. Yellow beige colored pellets were confirmed and, following manufacture's protocol, the virus was concentrated by centrifuge at 1500 g for 30 min at 4° C. Virus pellets were collected and resuspended in PBS solution and stored at −80° C. until used.

Viral Single Round Infection/Inhibition Assay of Pseduotyped HIV-1 System by C46 Transduced in MSCs:

In order to mimic the HIV infection system, HRST (CMV-GFP) was packaged with an HIV envelope, JRFL. The CD4+ cell line CEMx174 were treated with conditioned medium (CM) from the control (HRST-GFP, LZRS-GFP) or C46 (T-60, M218, and T-42) transduced MSC and infected with various MOI of concentrated pseudo HIV-1 viral-like particles produced by calcium phosphate method. After 48 hrs, cells were harvested and fixed with 4% PFA. Samples were analyzed for GFP(+) by BD FAC Verse™ flow cytometry at Tulane National Primate Research Center. GFP (+) flow analysis was conducted by FlowJo version 10 program.

Figure 10:
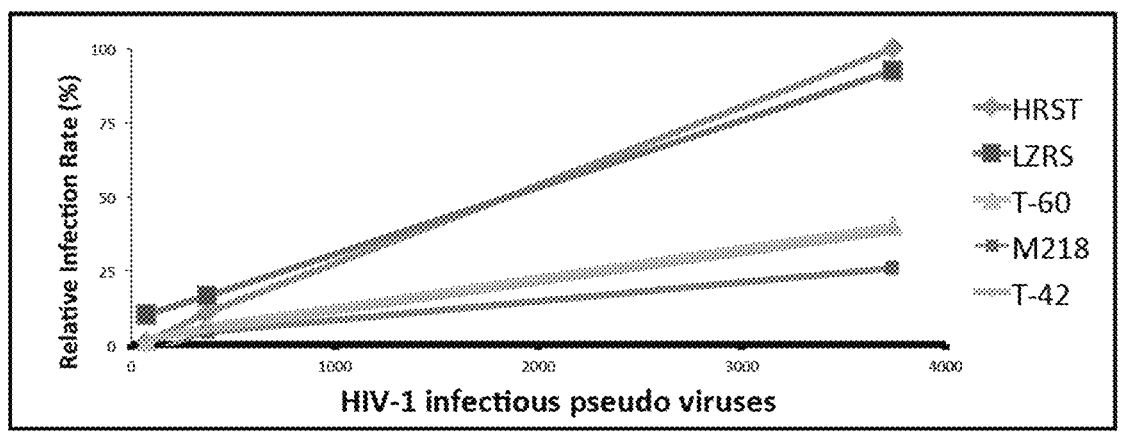
FIG. 10 displays a single round infection/inhibition assay in CEMx174 cells using conditioned media from MSC transduced with different inhibitors.

The resulting single round infection/inhibition assay is shown in FIG. 10. The CM from the control cells had the highest level of GFP expression (infection with the pseudoviral particles). Treatment with CM from the C46-transduced MSCs blocked infection. The level of GFP expression in the CEMx174 cells was graphed relative to the expression in the control population. Thus, the conditioned media from C46-transduced MSCs were able to block infection with HIV-1 pseudovirus in a single round inhibition assay.

Mesenchymal Stem Cell Differentiation Assay:

To test that the inhibitors do not disturb MSCs differentiation, osteogenic, adipogenic, and chondrogenic differentiation assay with StemPro® Osteogenesis Differentiation Kit, Gibco A1007201, A1007001, and A1007101 was performed on LZRS-GFP, LZRS-T60, HRST-GFP, M218, T42, and non-transduced RhMSCs. Assay procedure was followed manufacture's protocol. Briefly, cell number to be seeded for assay was $5 \times 10^3$ cells/cm$^2$ and $1 \times 10^4$ cells/cm$^2$ into 12 wells for osteogenic and adipogenic differentiation respectively. $1.6 \times 10^7$ viable cells/ml was plated by seeding 5-μl droplets of cell solution in the center of multi-well plate wells for classical stain for chondrogenic differentiation. Following around 21 days culture depends on cells growth, osteogenic, adipogenic, and chondrogenic differentiation were stained by alizarin red S, oil red o, and safranin o solution respectively. Stained cells were observed and taken pictures under bright field light microscope.

Example 4

The MSCs that expressed HIV inhibitor peptides in Examples 2 and 3 can be combined with antiviral drugs in vitro to assess the synergetic effects. PMPA (Tenofovir disoproxil fumarate, TDF or tenofovir) and FTC (Emtriva or Emtricitabine) are exemplary antiviral drugs whose synergetic effects with the above MSCs can be measured in an in vitro cell culture model.

For instance, CEMx174 cells can be infected with various MOI of Simian-HIV 89.6p or HIV strains. Then, MSCs can be treated with Mitomycin C, which is used to generate mitotically inactive the MSC feeder cells. The CEMx174 cells can then be co-cultured with the treated MSC for up to 14 days with or without additional antiviral drugs (e.g. 2 uM of PMPA and 1.5 uM FTC or others). The HIV replication in the CEMx174 cells can be monitored using p27 flow cytometry or ELISA, or RT-PCR, or other method. Inhibition of viral replication will be quantified by limiting dilution assay.

Alternatively, CEMx174 cells can be treated with conditioned medium from the control (HRST-GFP, LZRS-GFP) or C46 (T-60, M218, or T-42) transduced MSCs and combined with the PMPA and FTC (or other standard HIV drug). Then, CEMx174 cells are exposed to the HIV viral-like particles. Inhibition of the HIV infection of the CEMx174 cells is measured by GFP expression.

Additionally, the order of treatment can be varied such that infected CEMx174 cells are treated with the transduced MSCs before the antiviral drugs or co-administered with the antiviral drugs.

Example 5

Animal model testing using the MSCs that expressed HIV inhibitor peptides in Examples 2 and 3 alone or in combination with antiviral drugs can be performed with small and large animal models.

An exemplary small animal model is an immunodeficient mouse model. Table 1 lists many available mouse models and their advantages or disadvantages indicating that certain mouse models may be better candidates for animal testing.

TABLE 1

Exemplary immunodeficient mouse model

| Humanized Mouse Model | Cellular composition in reconstituted hu-mice | Advantages | Disadvantages |
|---|---|---|---|
| Hu-PBL SCID | T and B cells | Easy to generate<br>Can immediately be used after transfer of PBLs | No multilineage haematopoiesis<br>Limited time fram for experiments<br>Strong activation of T-cells<br>Emergence of xeno-reactive T-cells (GVHD) |
| Thy/Liv SCID hu | T cells<br>Single positive, double positive and double negative Thymocytes | Organoid of fetal thymus/liver tissue with sustained T-cell lymphopoiesis<br>Valuable to study certain pathogenic aspects | Surgical skills needed<br>Human fetal tissue needed<br>No multilineage hematopoiesis<br>Lack of CCR5 expression on intrathymic T progenitor cells |
| Rag2 $^{-/-}$γc $^{-/-}$ | T, B cells, Monocytes, Macrophages, NK cells, and DCs | Long term multilineage hematopoiesis<br>Specific antibody response to recall antigens<br>Suited to study HIV pathogenesis, HIV latency, gene therapy and novel anti-HIV treatment approaches | Delay between transplantation of human CD34+ cells and development of lymphoid systems of ~15 weeks |
| NOG or NSG | T, B cells, Monocytes, Macrophages, NK cells, and DCs | Higher reconstitution levels as compared to Rag mice<br>Suited to study HIV pathogenesis, HIV treatment, gene therapy approaches | Sensitive to irradiation |
| NOD/SCID-hu BLT & NOD/SCID γc $^{-/-}$ (NSG) BLT | T, B cells, Monocytes, Macrophages, NK cells, and DCs | Generation of adaptive immune responses<br>Suited to study HIV pathogenesis, HIV latency, gene therapy and novel anti-HIV treatment approaches | Two stop procedure for generating BLT mice<br>Surgical skills needed<br>Human fetal tissue needed |

The therapeutic potential of the stem cells in the humanized mouse models can be measured by analyzing the degree of human cell engraftment by flow cytometry of the peripheral blood mononuclear cells after they have been stained for panhuman markers such as CD45, CD3, CD4, CD8, CD14, and CD19.

Non-human primate models can be used for the large animal model testing. Such primate models would allow for the use of simian-HIV (S-HIV) infections. The S-HIV viral load in plasma of the animals can be measured using real time PCR. The therapeutic potential of the stem cells can be determined by analyzing the blood and tissue samples from infected primates for bio-distribution of MSCs, toxicity and peptide measurement.

Example 6

Figure 11A:
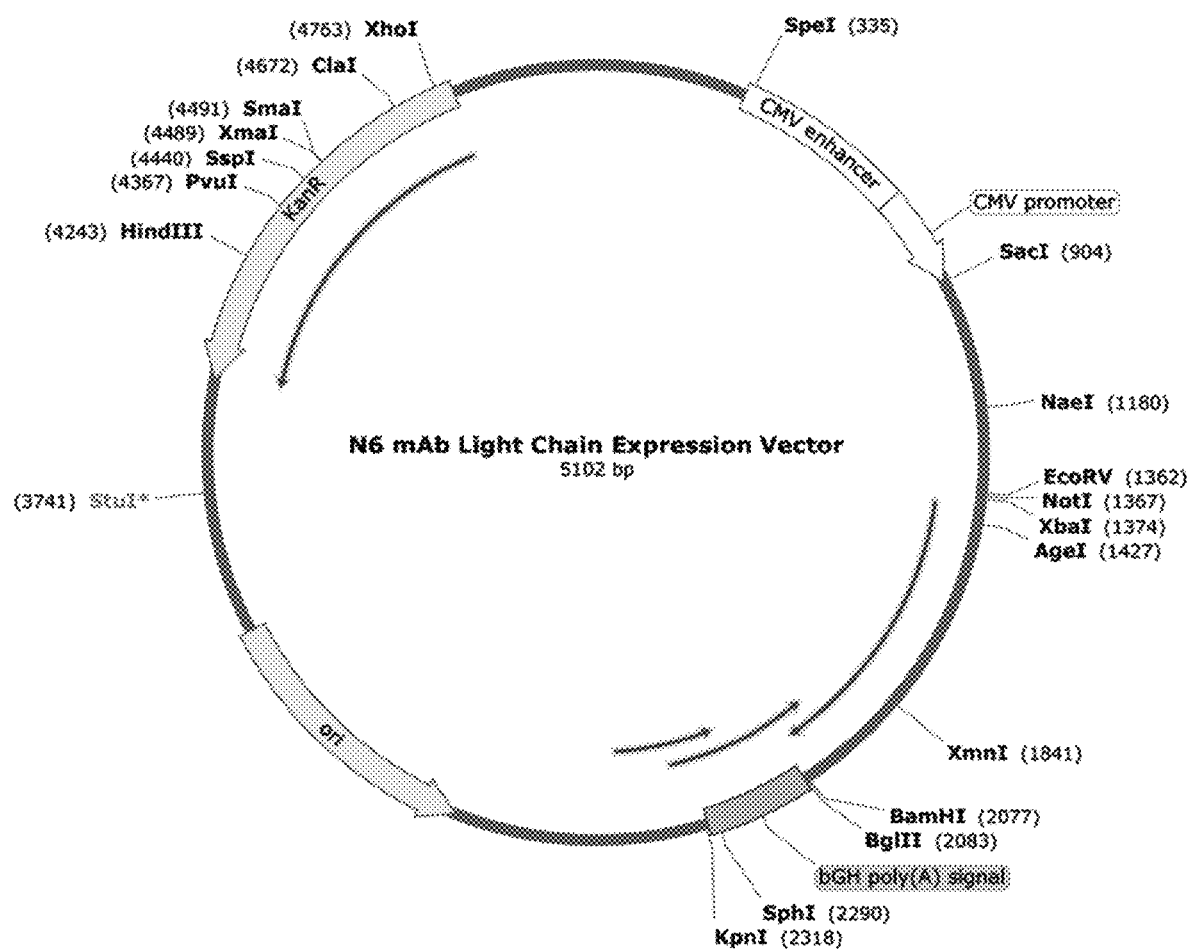
FIG. 11A-C displays the design of a number of vectors incorporating antibody inhibitors.
Figure 11B:
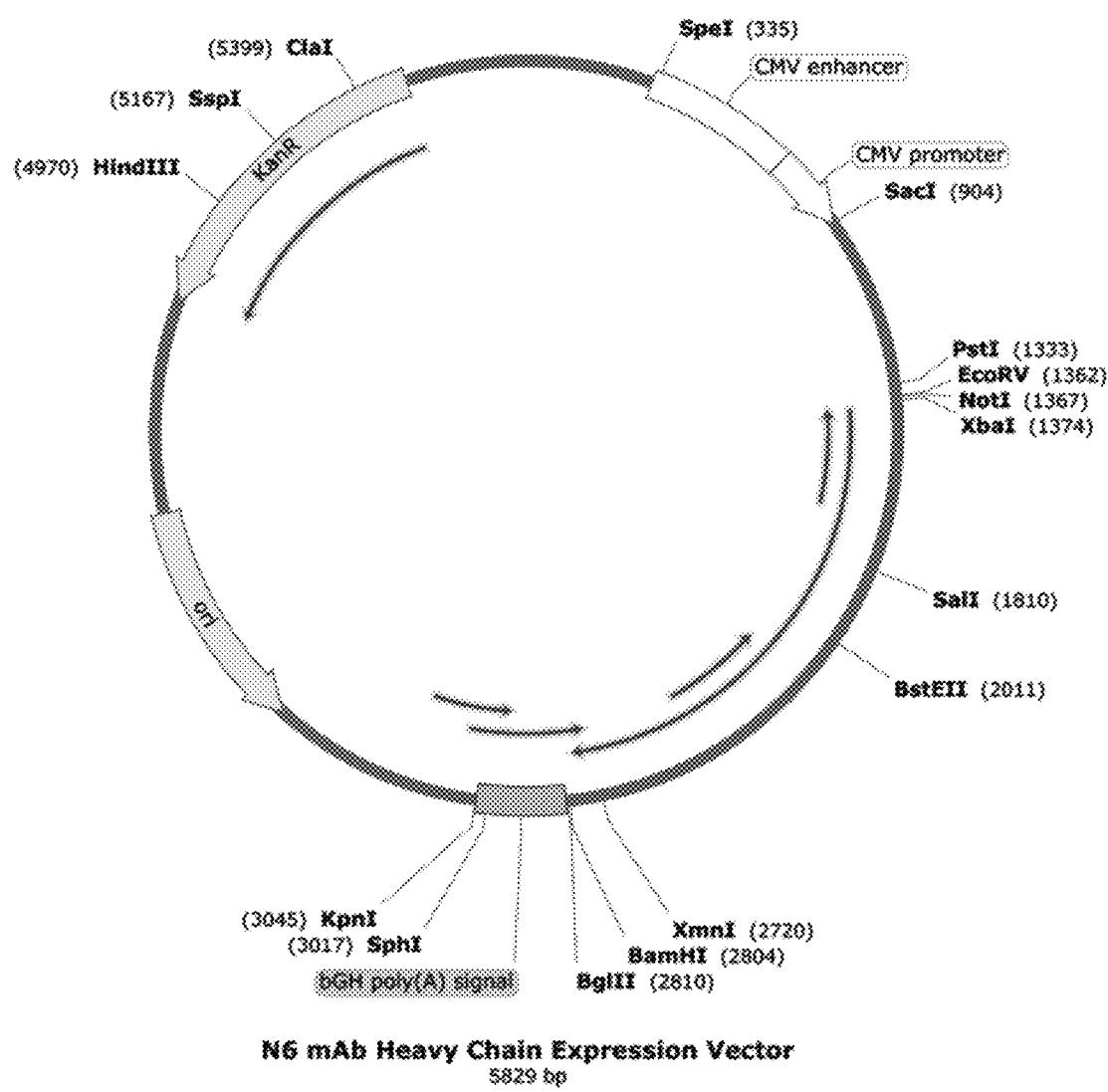
Figure 11C:
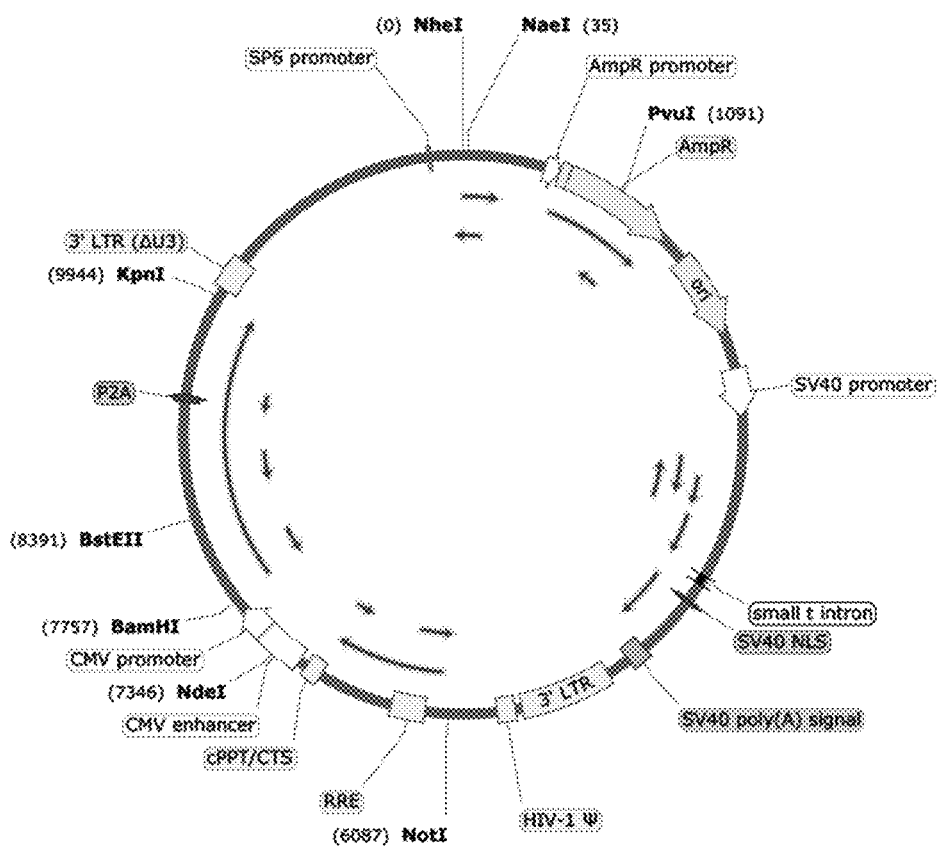

In addition to peptide inhibitors, antibody-based inhibitors can also be incorporated into the MSCs genome for long-term expression and treatment of virus-infected cells. Similar to the peptides, a variety of neutralizing antibodies were incorporated into vectors and expressed in cells. For the experiments involving antibody-based inhibitors, transient transfection of two expression vectors (plasmids encoding N6 mAb heavy and light chains) were used, each using a CMV early promoter to regulate expression (see vector maps in FIG. 11A-B). Alternatively, a lentiviral vector could have also been used to deliver both the N6 mAb H&L genes with a P2A self-cleaving element to separate the heavy and light chain proteins after expression (see FIRST map in FIG. 11C), much like it was used above with the protein inhibitors. Conditioned media from the transfected MSCs was used to inhibit HIV-1 viral replication. The effects for multiple NABs (B404, N6, 10E8v4, and/or 35022) are shown in FIGS. 12-13.

Figure 12:
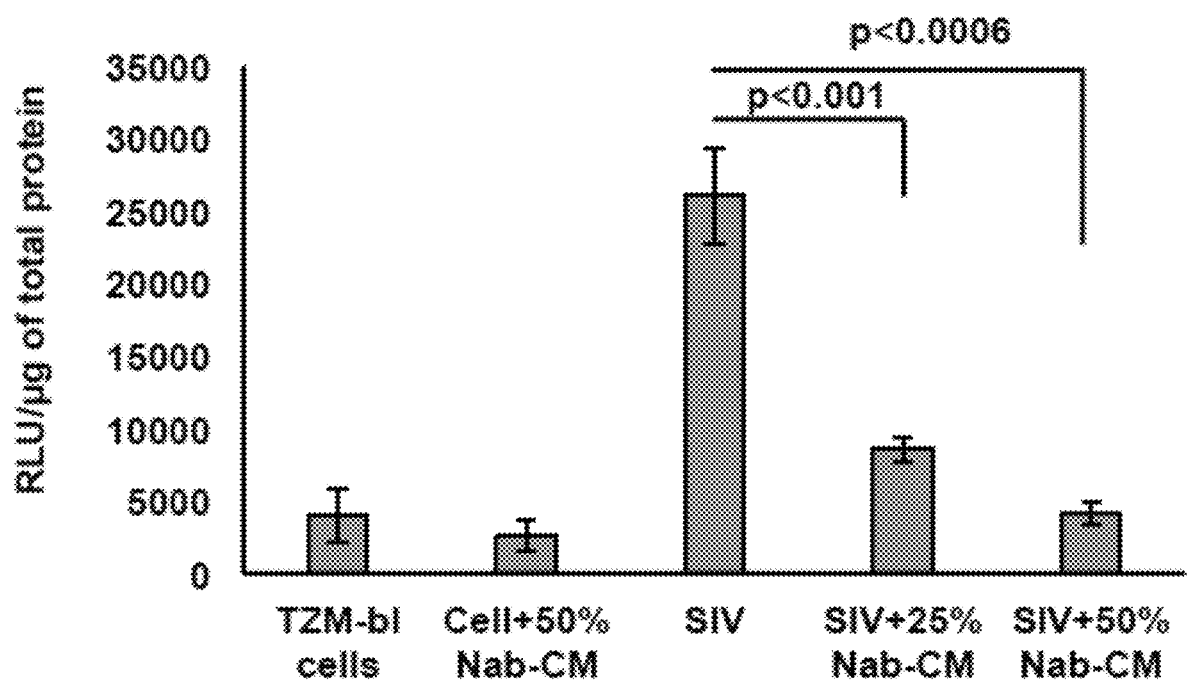

FIG. 12 shows viral-specific activation of the luciferase gene in TZM-bl cells. The TZM-bl cells ($2\times10^4$ cells/well) and SIVmac239 were pretreated with CM (50%, 25%, or none) for 2 hours at 37° C., and then mixed. After 72 hours, the cells were washed with PBS before being lysed with 1× passive lysis buffer. Firefly luciferase activity was then measured from clear lysates, as a percent of control. Cells challenged with SIV produce high levels of luciferase activity. However, when the cells were treated with CM containing B404 Nab, viral replication was significantly inhibited.

Figure 13:
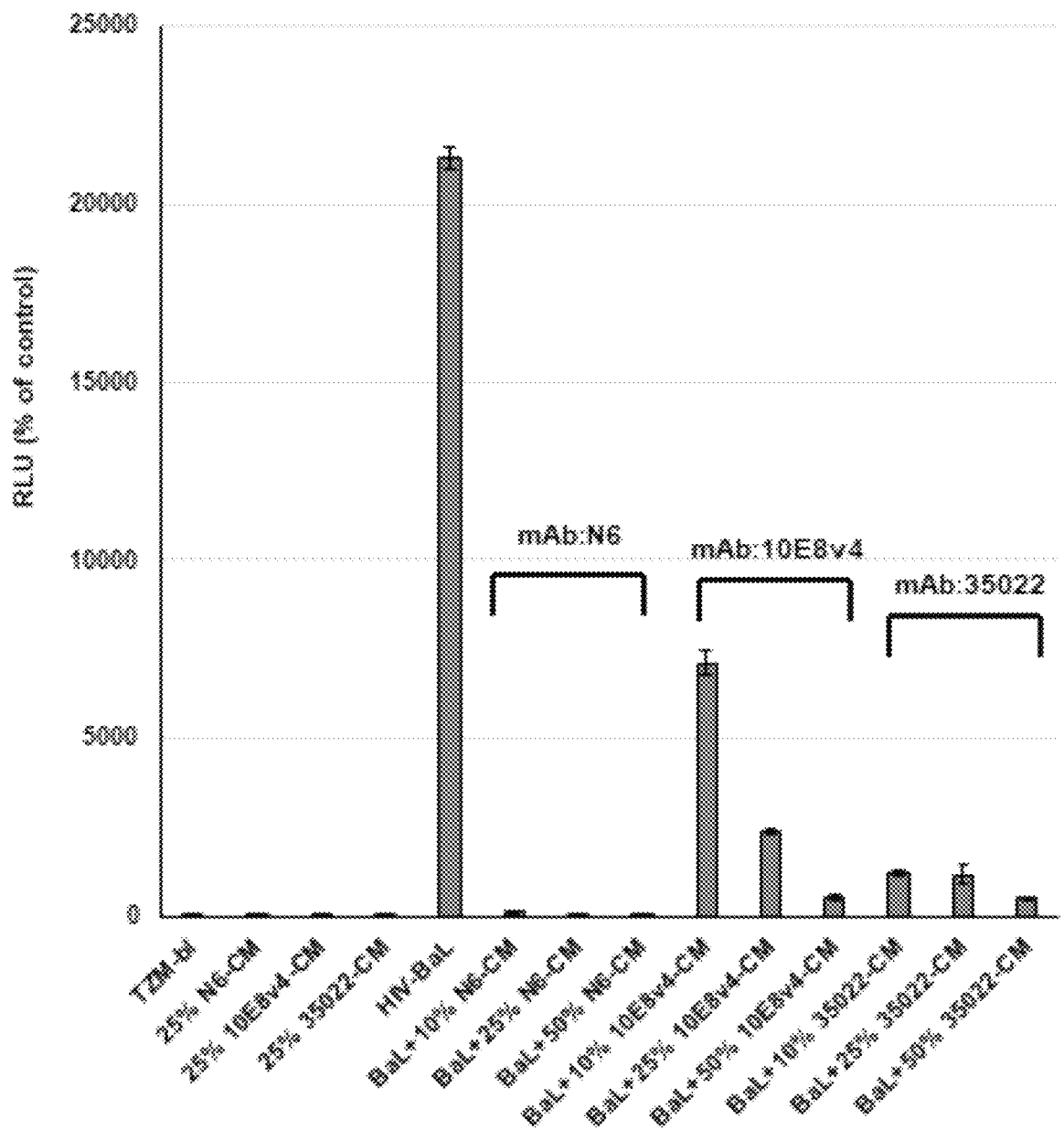

FIG. 13 displays varying concentrations (10%, 25%, and 50%) of conditioned media expressing N6, 10E8v4, and/or 35022 to inhibit viral infection of TZM-bl reporter cells. The TZM-bl cells were prepared as described above. The TZM-bl cells ($2\times10^4$ cells/well) and HIV-BaL (MOI=5) were treated with dilutions of NAB (10%, 25%, and 50%) for 2 hours at 37° C., and then mixed. After 72 hours, the cells were washed with PBS before being lysed with 1× passive lysis buffer. Firefly luciferase activity was then measured from clear lysates as percent of control.

As expected, CM containing NABs was able to inhibit the HIV infection in the TZM-bl reporter cells for both SIV and HIV-BaL. The inhibition data is very promising. The control cells maintained low levels of enzyme, but infection with HIV-BaL produce high levels of Luc activity, and pretreatment with the NAB, even when diluted to only 10% CM, potently inhibited viral replication. For example, with N6, Applicant was able to inhibit 99% of HIV infection with only 10% mixture of conditioned media. Other types of antibodies, or even combinations of antibodies, are expected to show similar success with the treatment of cells infected with HIV. This data shows that HIV can be treated using less complex and more accommodating methods that rely on MSCs expression of peptides and/or antibodies.

In view of the above experiments, it is clear that MSCs can carry a variety of genes for viral inhibitors to the local site of inflammation or virus infective cells. These inhibitors can be incorporated into many types of expression vectors, such as retroviral or lentiviral vectors, which are then transduced into the MSCs for expression at the site of inflammation and/or infection.

While certain novel features of this disclosure shown and described above are pointed out in the annexed claims, the disclosure is not intended to be limited to the details specified, since a person of ordinary skill in the relevant art will understand that various omissions, modifications, substitutions and changes in the forms and details of the disclosure illustrated and in its operation may be made without departing in any way from the spirit of the present disclosure. No feature of the disclosure is critical or essential unless it is expressly stated as being "critical" or "essential."

Furthermore, the above experiments and examples are not intended to limit the scope of the disclosure composition or methods to certain cells or animals.

The following references are incorporated by reference in their entirety.
WO2010053350
US20100226976
US20110027240

The invention claimed is:

1. A pharmaceutical composition, said composition comprising isolated mesenchymal stem cells (MSCs) wherein said isolated MSCs have been transfected with a lentiviral expression vector that is integrated into the genome of the isolated MSCs, wherein said lentiviral expression vector comprises a nucleic acid sequence encoding the full-length heavy and light chains of a single-chain antibody that is a human immunodeficiency virus (HIV) antiviral fusion inhibitor selected from the group consisting of N6, 10E8v4 and 35022, said lentiviral expression vector comprising a HIV-1 Ψ and, from 5' to 3', a Human cytomegalovirus (CMV) promoter, a nucleotide sequence encoding the heavy chain protein of the antibody, a nucleotide sequence encoding the light chain protein of said same antibody, and a P2A protease cleavage site separating said heavy and said light chain sequences, and conditioned media from the MSCs expressing the heavy and light chains inhibits HIV-1 infection.

2. The composition of claim 1, wherein said antiviral fusion inhibiting antibody is a neutralizing antibody.

* * * * *